US006632853B2

(12) United States Patent
Alkemper et al.

(10) Patent No.: US 6,632,853 B2
(45) Date of Patent: Oct. 14, 2003

(54) DENTAL COMPOSITES CONTAINING HYBRID FILLERS AND PROCESS FOR THEIR PRODUCTION

(75) Inventors: Jochen Alkemper, Viernheim (DE); Joachim Binder, Eggenstein-Leopoldshafen (DE); Harald Rentsch, Hanau (DE); Hans-Joachim Ritzhaupt-Kleissl, Walldorf (DE); Jürgen Hausselt, Germersheim (DE)

(73) Assignees: Degussa AG, Dusseldorf (DE); Forschungszentrum Karlsruhe GmbH, Karlsrube (DE)

( * ) Notice: Subject to any disclaimer, the term of this patent is extended or adjusted under 35 U.S.C. 154(b) by 0 days.

(21) Appl. No.: 09/938,832

(22) Filed: Aug. 27, 2001

(65) Prior Publication Data

US 2002/0045149 A1 Apr. 18, 2002

(30) Foreign Application Priority Data

Aug. 26, 2000 (DE) .......................... 100 42 050

(51) Int. Cl.⁷ .............................. C08F 2/46; A61K 6/08
(52) U.S. Cl. .................... 522/83; 522/100; 522/90; 522/170; 522/168; 522/101; 522/181; 522/182; 522/71; 522/74; 522/75; 522/76; 522/77; 522/81; 522/79; 522/82; 428/404; 428/402; 428/405; 428/406; 523/109; 523/115; 523/116; 523/119

(58) Field of Search .................... 522/100, 170, 522/101, 181, 71, 74–79, 81, 83, 90, 168, 182, 82; 523/109, 115, 116, 117; 428/402, 404, 405, 406

(56) References Cited

U.S. PATENT DOCUMENTS

| | | | |
|---|---|---|---|
| 4,217,264 A | | 8/1980 | Mabie et al. |
| 4,306,913 A | * | 12/1981 | Mabie et al. ............... 106/450 |
| 4,350,532 A | * | 9/1982 | Randklev ................. 106/31.95 |
| 4,381,918 A | * | 5/1983 | Ehrnford .................... 523/115 |
| 4,452,622 A | * | 6/1984 | Smyth .......................... 65/454 |
| 4,503,169 A | * | 3/1985 | Randklev .................... 523/117 |
| RE32,073 E | * | 1/1986 | Randklev .................... 523/117 |
| 4,707,504 A | * | 11/1987 | Walkowiak et al. ........ 523/109 |
| 5,426,082 A | | 6/1995 | Marsden |
| 5,707,440 A | * | 1/1998 | Hengchang et al. ........ 106/485 |
| 6,232,367 B1 | * | 5/2001 | Kobashigawa et al. ..... 523/116 |

FOREIGN PATENT DOCUMENTS

| | | |
|---|---|---|
| DE | 3421 157 | 12/1985 |
| DE | 3421157 A1 | 12/1985 |
| DE | 40 29 230 A1 | 3/1992 |
| DE | 35 87 890 | 2/1995 |
| DE | 40 29 230 | 3/1995 |
| DE | 43 34 211 | 4/1995 |
| DE | 43 34211 A1 | 4/1995 |
| DE | 196 03 196 A1 | 8/1997 |
| DE | 196 03 196 | 8/1997 |
| DE | 196 15 763 | 10/1997 |
| DE | 198 46 556 | 4/2000 |
| EP | 0 048 681 | 3/1982 |
| EP | 0 530 926 | 3/1993 |

* cited by examiner

Primary Examiner—James J. Seidleck
Assistant Examiner—Sanzal L McClendon
(74) Attorney, Agent, or Firm—Smith, Gambrell & Russell LLP

(57) ABSTRACT

Dental composites containing hybrid fillers and process for their production. Dental compounds are disclosed which contain two- or multi-phase inorganic fillers in an organic polymer matrix. These are characterized by improved abrasion resistance.

40 Claims, No Drawings

DENTAL COMPOSITES CONTAINING HYBRID FILLERS AND PROCESS FOR THEIR PRODUCTION

INTRODUCTION AND BACKGROUND

The present invention relates to a dental material and a process for producing this material. In a further aspect, the invention also relates to novel hybrid fillers.

The invention relates in particular, to dental materials formed from a polymerizable binder, for example ethylenically unsaturated monomers, epoxides, ormocers, liquid crystalline monomers, oxethanes, spiroorthoesters or spiroorthocarbonates, a catalyst for cold-, heat- or photo-polymerization and 0.5–75 wt. % in relation to the dental material of a hybrid filler (A) together with 0.0–95 wt. % in relation to the dental material of other fillers (B) and 0.0–2 wt. % of other conventional additives.

Because of the possible health risks involved in using materials containing mercury (amalgams) for tooth restoration, the search for new mercury-free preparations for this purpose has intensified.

Porous glass ceramics are known from U.S. Pat. No. 5,426,082, which are used to produce special catalysts. The ceramics cited there should have a minimum pore volume of >2000 mm$^3$/g. These high pore volumes render these materials unsuitable for use as fillers in dental materials, as the resulting fillings are of low strength.

The filled inorganic porous particles disclosed in EP 48 681 are fillers consisting of amorphous glass. However, a disadvantage of the dental materials cited here is that, because of their structure and size, the particles of the filler, when applied, may penetrate the lungs, presenting the risk of an illness comparable to asbestosis.

EP-A 0 530 926 discloses dental compounds composed of a polymerizable monomer and an inorganic filler, which consist of 20–80 wt. % spherical inorganic oxide particles with an average particle size of 1.0 to 5.0 μm and 80–20 wt. % of spherical inorganic oxide particles with a particle size in the range 0.05 μm minimum and less than 1.0 μm, at least 5 wt. % of the latter component being in the range 0.05 to 0.2 μm. The inorganic particles are exclusively spherical particles of inorganic oxides of silicon, zirconium, aluminum and titanium or mixed oxides of elements from the main Groups I–IV of the Periodic Table of Elements with silicon. The spherical particles are produced e.g. by hydrolytic polymerization of alkoxysilanes and may also be surface-treated e.g. with γ-methacryloxypropyl trimethoxysilane. The fillers cited here consist optionally of mixtures of particles produced from a single material.

DE 196 15 763 discloses amorphous silicon dioxide glasses loaded with monomers. The glasses are built up homogeneously, and so cannot be described as hybrid fillers according to the invention.

DE 198 46 556 proposes porous glass ceramics as filler components. A glass ceramic is deemed here to be a partially crystalline material, which is built up of amorphous SiO$_2$ compartments, in which compartments of crystalline oxides according to the invention are embedded (see also Ullman's Encyclopaedia of Industrial Chemistry 5$^{th}$ Ed., A12, p. 433 ff). This is therefore another mixed oxide, in other words a material built up homogeneously. The dental composites proposed hitherto have achieved the strength of amalgam fillings, and thus it is possible to use these composites on the chewing surface of teeth. However, in addition to strength, the optical quality of the composite must also be considered, which should merge as unobtrusively as possible with the surrounding natural teeth. The filler must also have sufficient radiopacity to allow the dentist to check the correct placing of the filling.

An object of the present invention was therefore to develop another dental filler, which satisfies the above criteria as well as possible.

In particular, the dental material should have improved abrasion resistance coupled with comparably good polymerization shrinkage and high strength. In addition, the polymer matrix should be prevented as far as possible from being detached from the inorganic filler by hydrolytic splitting. The dental material should also be radiopaque if desired and should be transparent enough to allow it to be inserted into the tooth cavity and light-cured in one step.

A still further object of the invention is to provide particular fillers, which are suitable for use in dental materials according to the invention.

Insofar as they relate to a dental material, the above and other objects of the invention can be achieved by a dental material as described herein.

The above and other objects relating to the particular filler of the invention can also be achieved as described herein below.

SUMMARY OF THE INVENTION

The dental material of the present invention is based on polymerizable binder, for example ethylenically unsaturated monomers, epoxides, ormocers, liquid crystalline monomers, oxethanes, spiroorthoesters or -carbonates, a catalyst for cold-, heat- and/or photo-polymerization and 0.5–75 wt. % in relation to the dental material of a hybrid filler (A) together with 0.0–95 wt. % in relation to the dental material of other fillers (B) and 0.0–2 wt. % of other conventional additives (C). The hybrid filler (A) of the invention comprises a sintered heterogeneous mixture of fillers (B) and one or more primary particles of oxides, fluorides, sulfates, phosphates, borides, nitrides, carbides and/or silicides of elements of Groups I to V of the Periodic Table of Elements. Superior dental materials are achieved in an unforeseeable manner in accordance with the invention. Reduced abrasion in particular is a striking feature of this dental material, due to the fact that the size of microfractures in the inorganic part of the filler is restricted, as each ends at the phase boundaries of the individual particles which have been sintered together (fracture control). However, filler components which are produced wholly from one material have a fracture which extends through the whole body of the filler. This increases the tendency for larger filler components to break off and thus also increases abrasion.

The relationship between the sizes of the particles in the dental material (hybrid filler (A) and filler (B) not contained in (A)) is variable. It should be established in such a way that the filler is packed as densely as possible, on the one hand to minimize polymer shrinkage and on the other to increase the strength of the dental material.

The optimum size of hybrid filler (A) according to the invention in the dental material is 1–200 μm, in particular 3–90 μm.

The ratio of the size of fillers (B) in hybrid filler (A) to one or more primary particles of oxides, fluorides, sulfates, phosphates, borides, nitrides, carbides and/or silicides of elements of Groups I to V of the Periodic Table of Elements can be chosen freely by the person skilled in the art depending on what is required of the hybrid filler and on practicability. A size ratio in the range >1:1–1:20000, preferably 1:10–1:1000, is preferred.

The ratio of the mass of fillers (B) in hybrid filler (A) to one or more primary particles of oxides, fluorides, sulfates, phosphates, borides, nitrides, carbides and/or silicides of elements of Groups I to V of the Periodic Table of Elements can be within ranges that seem obvious to the person skilled in the art from a reading of this application. A range of 25–75 wt. % of (B) in relation to the total weight of (A) is preferred.

The optionally porous components of hybrid filler (A) (filler (B) and primary particles) can be sintered together, depending on the temperature and sintering time, until the filler has been built up compactly and no longer contains any pores. Sintering for a shorter time at lower temperatures allows the pore volume and pore diameter to be chosen advantageously so as to allow special monomers to permeate the pores and form an internal monomer distribution. A filler (A) is therefore preferred, which has a pore volume of >0–2000 mm$^3$/g, preferably 50–1500 mm$^3$/g. It is also preferable for the pore diameter of hybrid filler (A) to be >0–1000 nm, in particular 20–100 nm.

As indicated above, the porous hybrid filler (A) can also be loaded with polymerizable or polymerized, for example ethylenically unsaturated monomers, epoxides, ormocers, liquid crystalline monomers, oxethanes, spiroorthoesters or spiroorthocarbonates. This preferred embodiment serves to form a polymer network in the filler, which is capable of reacting on the exo-side with the organic polymers present in the dental matrix. A chemical interleaving of the organic polymer matrix with the inorganic filler is thus achieved, which is very difficult to destroy. This prolongs the lifetime of fillings. An advantageous procedure is described for example in DE 198 46 556. The procedure described there applies here accordingly.

Hybrid fillers (A) which contain primary particles of oxides, fluorides, sulfates and/or phosphates of elements of Groups I to V of the Periodic Table of Elements perform particularly well.

In a further development the invention relates to a process for the production of dental materials based on polymerizable binder, for example ethylenically unsaturated monomers, epoxides, ormocers, liquid crystalline monomers, oxethanes, spiroorthoesters or carbonates, a catalyst for cold-, heat- or photo-polymerization and 0.5–75 wt. %, preferably 25–75 wt. % in relation to the dental material of a hybrid filler (A) and 0.0–95 wt. % in relation to the dental material of other fillers (B) and 0–2 wt. % of other conventional additives (C), characterised in that hybrid filler (A) is produced by sintering a mixture of fillers (B) and one or more primary particles of oxides, fluorides, sulfates, phosphates, borides, nitrides, carbides and/or silicides of elements from Groups I to V of the Periodic Table of Elements.

The sintering temperature can be varied as already indicated above, the sintering temperature having an impact on the pore volume and the pore characteristics. The temperatures to be chosen depend on the educts. They are generally >500° C. and <1500° C., preferably >700° C. and <1200° C.

Before sintering, the hybrid filler (A) can be spray dried at <200° C., preferably <130° C. The person skilled in the art is sufficiently aware of suitable spray drying processes (Lukasiewicz, L. S.: J.Amer.Ceram. Soc. 1998, 72(4), 617–624). The mixture to be used for spray drying can be produced by processes known to the person skilled in the art (e.g. e.g. M. Gugleilmi et al., J. Non-Cryst. Solids 1988, 100, 292–297).

Particularly suitable fillers are obtained if the pores of porous hybrid fillers (A) are loaded with polymerizable or polymerized, for example ethylenically unsaturated, monomers, epoxides, ormocers, liquid crystalline monomers, oxethanes, spiroorthoesters or -carbonates. This can be achieved by charging the pores with gaseous or liquid monomers and then optionally polymerizing the monomers in the filler. The loaded hybrid filler (A) can therefore optionally be incorporated into the dental compound in ready-polymerized form or the monomer components present in the filler can be polymerized in the cavity at the same time as the dental compound. Both procedures are evaluated thoroughly in DE 198 46 556. The procedure described there applies here accordingly.

A further development of the invention relates to a dental material which can be obtained by a process according to the invention as described above.

The invention also relates to the hybrid fillers (A) themselves, which are characterized in that they consist of a sintered heterogeneous mixture of fillers (B) and one or more primary particles of oxides, fluorides, sulfates, phosphates, borides, nitrides, carbides and/or silicides of elements of groups I to V of the Periodic System.

Hybrid fillers (A) preferably have the size, size ratio etc. properties described above for this material. It is preferably produced by a sintering process as indicated further above. Hybrid filler (A) is preferably used in dental materials, but can in principle be used to reinforce plastics in general.

In a particularly preferred development of the invention, the porous hybrid filler (A) may consist of a sintered heterogeneous mixture of fillers (B) and one or more primary particles of oxides, fluorides, sulfates, phosphates, borides, nitrides, carbides and/or silicides of elements of Groups I to V of the Periodic Table of Elements and may be loaded with polymerizable or polymerized, for example ethylenically unsaturated monomers, epoxides, ormocers, liquid crystalline monomers, oxethanes, spiroorthoesters or -carbonates.

Similarly, this filler can be produced by a process in which hybrid filler (A) is loaded with gaseous or liquid monomers and then optionally polymerized in the filler. It can then be incorporated e.g. into the dental compound. Such porous hybrid fillers (A), which are loaded with polymerized or polymerizable; for example ethylenically unsaturated, monomers, epoxides, ormocers, liquid crystalline monomers, oxethanes, spiroorthoesters or -carbonates, are particularly suitable for the production of dental materials, but can be used to reinforce plastics in general.

The Binder

All binders based on polymerizable, ethylenically unsaturated monomers, which are familiar to the person skilled in the art for this purpose, may be used as binders for the dental material. Polymerizable monomers which may successfully be used include those containing acrylic and/or methacrylic groups.

These include, in particular, esters of $\alpha$-cyanoacrylic acid, (meth)acrylic acid, urethane (meth)acrylic acid, crotonic acid, cinnamic acid, sorbic acid, maleic acid and itaconic acid with mono- or divalent alcohols; (meth)acrylamides such as e.g. N-isobutylacrylamide; vinylesters of carboxylic acids such as e.g. vinylacetate; vinyl ethers such as e.g. butylvinylether; mono-N-vinyl-compounds such as N-vinylpyrrolidone; and styrene and its derivatives. The mono- and polyfunctional (meth)acrylic acid esters and urethane (meth)acrylic acid esters listed below are preferred in particular.

(a) Monofunctional (meth)acrylate methyl(meth)acrylate, n- or i-propyl(meth)acrylate, n-, i- or tert.-butyl(meth)acryate and 2-hydroxyethyl (meth)acrylate.

(b) Difunctional (meth)acrylates Compounds of the general formula:

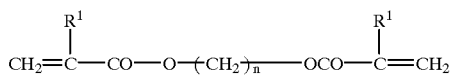

Wherein $R^1$ is hydrogen or methyl and n is a positive integer from 3 to 20, such as e.g. di(meth)acrylate of propanediol, butanediol, hexanediol, octanediol, nonanediol, decanediol and eicosanediol, Compounds of the general formula:

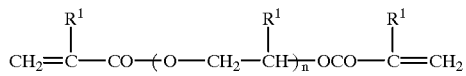

Wherein $R^1$ is hydrogen or methyl and n is a positive integer from 1 to 14, such as e.g. di(meth)acrylate of ethylene glycol, diethylene glycol, triethylene glycol, tetraethylene glycol, dodecaethylene glycol, tetradecaethylene glycol, propylene glycol, dipropylene glycol and tetradecapropylene glycol; and glycerine di(meth)acrylate, 2,2'-bis[p-(γ-methacryloxy-β-hydroxypropoxy)-phenyl propane] or bis-GMA, bisphenol-A-dimethacrylate, neopentylglycoldi(meth)acrylate, 2,2'-di(4-methacryloxypolyethoxyphenyl) propane with 2 to 10 ethoxy groups per molecule and 1,2-bis(3-methacryloxy-2-hydroxypropoxy)butane.

(c) Tri- or polyfunctional (meth)acrylates trimethylolpropanetri(meth)acrylate and pentaerythritol-tetra(meth)acrylate.

(d) Urethane(meth)acrylates

Reaction products of (meth)acrylate monomers containing 2 mol hydroxyl groups with one mol diisocyanate and reaction products of a urethane polymer having two NCO terminal groups with a methacrylic monomer, which has a hydroxyl group as e.g. represented by the general formula:

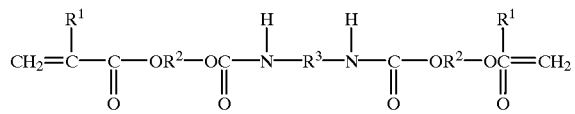

Wherein $R^1$ means hydrogen or a methyl group, $R^2$ represents an alkylene group and $R^3$ an organic group.

Monomers which can be used particularly advantageously in the dental material according to the invention include, above all, 2,2-bis-4-(3-methacryloxy-2-hydroxypropoxy)-phenyl propane (Bis-GMA), 3,6-dioxaoctamethylene dimethacrylate (TEDMA), and/or 7,7,9-trimethyl-4,13-dioxo-3,14-dioxa-5,12-diaza-hexadecane-1,16-dioxy-dimethacrylate (UDMA).

A description of the epoxides is given for example in DE 961 48 283 A1.

The term ormocers describes organically modified polysiloxanes such as those listed for example in DE 41 33 494 C2 or DE 44 16 857 and which can be used for dental compounds. Liquid crystalline dental monomers are disclosed in EP 0 754 675 A2. Oxethanes as dental monomers are disclosed in U.S. Pat No. 5 750 590 and DE 951 06 222 A1. Spiroorthocarbonates are disclosed for example in U.S. Pat. No. 5 556 896. The cited monomers are used either alone or in the form of a mixture of several monomers. All the above documents are relied on and incorporated herein by reference.

The Catalyst

The dental material can be polymerized under the influence of heat, cold or light depending on the type of catalyst used. The known peroxides such as dibenzoyl peroxide, dilauroyl peroxide, tert.-butyl peroctoate or tert.-butyl perbenzoate can be used as catalysts for heat-polymerization, but α,α'-azo-bis(isobutyroethylester), benzopinacol and 2,2'-dimethylbenzopinacol are also suitable.

Benzophenone and its derivatives as well as benzoin and its derivatives for example, can be used as catalysts for photo-polymerization. Other preferred photo-sensitizers are α-diketones such as 9,10-phenanthrene quinone, diacetyl, furile, anisile, 4,4'-dichlorobenziles and 4,4'-dialkoxybenziles, camphor quinone is preferred in particular. Photo-sensitizers are preferably used together with a reducing agent. Examples of reducing agents are amines such as cyanethylmethylaniline, dimethylaminoethylmethacryate, triethylamine, triethanolamine, N,N-dimethylaniline, N-methyldiphenylamine, N,N-dimethyl-sym.-xylidine and N,N-3,5-tetramethylaniline and 4-dimethylaminobenzoic acid ethylester. Radical-supplying systems e.g. benzoyl- or lauroylperoxide together with amines such as N,N-dimethyl-sym.-xylidine or N,N-dimethyl-p-toluidine are used as catalysts for cold polymerization. Dual curing systems can also be used for catalysis e.g. photo-initiators with amines and peroxides.

Mixtures of UV-light curing catalysts and catalysts which cure in visible light may be used as photo-catalysts.

The quantity of these catalysts in the dental material is normally between 0.01 and 5 wt. % The dental material according to the invention is preferably used as a tooth filling material. Tooth filling materials are also produced as two-component materials, which cold cure after mixing. The composition is similar to that of light-curing materials, but instead of photo-catalysts, e.g. benzoylperoxide is incorporated into one paste and e.g. N,N-dimethyl-p-toluidine is incorporated into the other. Mixing approximately equal quantities of the two pastes, produces a tooth filling material which cures in a few minutes.

If the amine is omitted from the latter materials and e.g. benzyl peroxide only is used as a catalyst, a heat-cured dental material is obtained, which can be used to produce an inlay or dentures. To produce an inlay, an impression is made of the cavity in the patient's mouth and a plaster model is produced. The paste is inserted into the cavity of the plaster model and the whole model is polymerized in a pressurised container under the influence of heat. The inlay is removed, processed and then cemented into the cavity in the patient's mouth.

The Dental Material

Dental material according to the invention means materials for tooth restoration such as fillings, inlays or onlays, fixing cements, glass ionomer cements, compomers, veneer materials for crowns and bridges, materials for dentures, dentine bondings, filling materials, root filling materials, or other materials for prosthetic, preservative and preventive dental care. In particular the term dental material also includes composites for use in dental care and dentistry, sealants, self-curing composites, core build-up materials, veneer plastics, highly filled and normally filled dual cements and normally filled fluoridated tooth coatings. In the polymerized state, the ratio of parts by weight of polymer to hybrid filler (A) to filler (B) in the dental fillers according to the invention can be in the range 10–80 to 20–70 to 1–30, preferably 30–50 to 30–60 to 5–20 (100 in total).

Filler B

All fillers familiar to the person skilled in the art as dental materials (e.g. for the improvement of radiopacity, viscosity, polishability, transparency, strength, refractive index) may be used as (B). To achieve even greater radiopacity fillers can be used such as those disclosed e.g. in DE-OS 35 02 594, (incorporated herein by reference) having an average primary particle size which may not exceed 5.0 $\mu$m. Optionally, small quantities of microfine, pyrogenic or wet-precipitated silica can be incorporated into the dental material as filler (B). Other possibilities are: Apatite according to EP 0 832 636 and/or particles according to DE 195 08 586 and/or DE 41 23 946, as well as glass ceramics according to DE 198 46 556 and/or zeolites according to DE 198 29 870 or WO 98/49997. All these publications are relied on and incorporated herein by reference.

Glass, $TiO_2$, zirconium oxide or fluoroapatite particles are preferably used as filler (B).

The size of the particles is generally between 0.1 and 20 $\mu$m, preferably between 0.5 and 5 $\mu$m. The shape of the particles is of little significance. They can range from irregular or chipping-shaped to plate-like, rod-shaped or spherical. The particles can be amorphous, partially crystalline or fully crystalline, compact or porous.

It can also equally consist of several components as for example, in a core-shell structure. For the production of these particles (B), refer to the relevant known processes which are dealt with in the above-mentioned literature.

Additives C

For the purposes of the invention, additives are deemed to be all additives familiar to the person skilled in the art, which can be incorporated into dental compounds to improve their quality. These include in particular dyes, emulsifiers etc.

Hybrid Filler A

As already mentioned, hybrid filler (A) is produced by sintering together filler (B) and one or more oxides, fluorides, sulfates, phosphates, borides, nitrides, carbides and/or suicides of elements of Groups I to V of the Periodic Table of Elements. This produces a heterogeneous mixture of fillers (B) in the named inorganic compounds (primary particles sintered together) as separate particles, filler (B) being randomly distributed amongst the particles. The use of all types of silica is particularly preferred for this. A summary of possible silicas and methods for producing them is given in Ullmans Enzyklopädie der technischen Chemie, [Ullmans Encylcopaedia of Industrial Chemistry] 1982, 4$^{th}$ edition, vol. 21, p. 439 ff. Aerosil® is preferred in particular as a sintering material for embedding the fillers (B). A summary of advantageous types of Aerosil® is given in: Technical Bulletin Pigments, Basic Characteristics of Aerosil®, Number 11, Edition 4, Degussa-Hüls AG.

The primary particles are smaller than those of the fillers (B) and preferably 1 to 200 nm, in particular 5 to 50 nm in diameter. Various primary particles can be sintered together with the fillers (B). The shape of the primary particles is not significant for this—as with fillers (B). These can also be amorphous, partially crystalline or crystalline.

Elements

Elements of Groups I to V according to the invention are deemed to be all elements of the corresponding main or subsidiary groups of the Periodic Table of Elements, with the exception of carbon, nitrogen, phosphorus, arsenic, antimony, copper, cadmium and mercury. Elements such as silicon, tin, zirconium, titanium and zinc are preferred in particular.

Modification of Fillers (A) and (B)

There may be further modifications of fillers (A) and/or (B) as follows: Bactericides may be implemented in the porous hybrid fillers (A). Hesperidin, naringenin, quercetin, anisic acid, acetyl coumarin, sitosterol, caryophyllene and caryophyllene oxide in particular are deemed to be bactericides. These compounds can be incorporated into the pores of hybrid filler (A) by the process disclosed in U.S. Pat. No. 4,925,660.

The inner and/or outer surface of a porous hybrid filler (A) and the inner and/or outer surface of filler (B) can preferably optionally be chemically modified before embedding in the dental material using surface materials familiar to the person skilled in the art. This serves amongst other things to a) increase mechanical stability and hydrophobic properties and b) further improve the coupling of the inorganic filler to the organic matrix.

In a particular embodiment the filler (A and/or B) is subsequently coated with silanes of the general formula RSi(OX)3, wherein R is an alkyl group containing 1 to 18 C atoms and X is an alkyl group containing 1 or 2 C atoms, and/or metal oxides. Trimethylchlorosilane in particular is used to increase stability and hydrophobic properties, as described in Koyano, K. A.; Tatsumi, T.; Tanaka, Y.; Nakata, S. J. Phys. Chem. B 1997, 101 p. 9436 and Zhao, X. S; Lu, G. Q., J. Phys. Chem. B 1998, 102, p. 1156. If a silane is used for subsequent coating it is useful if it is used in a quantity of about 0.02 to 2 wt. % of silane, calculated as $SiO_2$ in relation to the weight of filler (A) or (B). Particularly advantageous agents for subsequent coating include (CH3) 3SiCl, methyltriethoxysilane, ethyltriethoxysilane, octyltriethoxysilane, octadecyl-triethoxysilane, mono- or polyfluoroalkylethoxysilane and also silanes with functionalised organo groups, which allow subsequent further modification by covalent bonding in the known way. In the latter case such organotrialkoxy-silanes are preferred in view of the use according to the invention of particles as fillers in polymeric or polymerisable systems, which have such functional groups, with which a covalent bonding into the polymeric material can be achieved. Examples of this are trimethoxyvinylsilane, $H_2C=C(CH_3)CO_2(CH_2)_3Si(OCH_3)_3$, triethoxyvinylsilane, and 3-glycidoxypropyl-trimethoxysilane, as well as silanes with inorganic groups carrying hydroxyl, carboxyl, epoxy and carboxylic acid ester groups. The fillers modified in this way are bonded into the dental material by working the fillers into the dental material and polymerizing them subsequently during the actual curing of the dental material.

An advantage of the dental compound according to the invention is that the colour, transparency and radiopacity can be determined solely by the composition of hybrid filler (A) and/or filler (B). Optionally however, other metal oxides can be used for post-coating, preferably in a quantity of 1 to 100 wt% preferably 10 wt. %, in relation to the metal oxide content, of non post-coated fillers (A) and (B).

Preferred metal oxides, which can be used for post-coating are $TiO_2$, $Fe_2O_3$ and/or $ZrO_2$. In another useful embodiment, filler (A) and/or (B) is additionally covered with a layer of a polymerizable organic binder, based on mono- or polyfunctional (meth)acrylates and/or reaction products of isocyanates and methacrylates containing OH groups.

The possibility of varying the type and quantity of fillers (A) and/or (B) according to the invention therefore allows the refractive index of the fillers to be adapted to the refractive index of the polymer environment. This is the only way to ensure that the dental material as a whole is transparent enough to allow it to be cured as required in one piece in a tooth cavity. There is no need for laborious sequential application and curing of the dental material. Oxides preferred for this purpose are $TiO_2$, $ZrO_2$, BaO and $WO_3$. $ZrO_2$ is preferred in particular.

As with the modification of the refractive index, the ideal radiopacity of filler (A) and/or (B) can also be set through the choice of starting material. Oxides preferred for this purpose are $TiO_2$, $ZrO_2$, and BaO. $ZrO_2$ is preferred in particular.

The type of filler according to the invention is therefore responsible for achieving a surprisingly high degree of reinforcement coupled with low abrasion in the dental compounds, as a result of which they can be used on the chewing surfaces of teeth in a similar way to the known amalgam fillings.

The invention is explained by the following examples.

EXAMPLES

1. Aerosil/glass Particles 1.1 Production of particles containing 25 wt. % glass For the synthesis of hybrid particles, which consist of at least two different fractions, an $SiO_2$-sol(particle size approx. 20 nm) and a glass suspension (particle size approx. 1 μm) are prepared. To produce the $SiO_2$ sol, Aerosil 90® is worked into water using an Ultraturrax mixer. The sol is placed in a shaker overnight. The glass is suspended in water by electrostatic stabilization. The $SiO_2$ sol and the glass suspension are mixed in a ratio Aerosil 90®:glass=3:1. By spray drying at temperatures below 200° C. and subsequent calcination, spherical hybrid particles are obtained in which the glass particles are distributed virtually homogeneously in the Aerosil matrix.

1.2 Variation of the glass content

To produce powders with varying glass contents, $SiO_2$ sols and glass suspensions are mixed in the desired proportions. After spray drying and calcination at 750° C., powders are obtained which differ in density, specific surface, specific pore volume and pore size, depending on the glass content.

| Aerosil (Silica) Content [wt. %] | Glass Content [wt. %] | Density [g/cm3] | Specific Surface] [m²/g] | Spec. pore vol. [mm³/g] | Spec. pore Size [nm] |
| --- | --- | --- | --- | --- | --- |
| 90 | 10 | 2.31 | 74 | 1628 | 55 |
| 75 | 25 | 2.38 | 62 | 1510 | 57 |
| 50 | 50 | 2.46 | 45 | 1045 | 72 |
| 25 | 75 | 2.61 | 25 | 720 | 113 |
| 10 | 90 | 2.72 | 12 | 407 | 180 |
| 0 | 100 | 2.80 | 3 | 166 | 22 |

The influence of the glass content can be summarized as follows:

There is a linear change in density depending on the percentage by volume of glass.

There is a virtually linear reduction in specific surface and specific pore volume depending on the percentage by mass of glass.

The pore size depends greatly on the glass content.

1.3 Varying the calcination temperature

The material properties of the porous hybrid particles can be varied not only through the glass content, but also through the calcination temperature and/or time. For these investigations hybrid powders containing 10 wt. % and 25 wt. % glass were synthesized and then calcined both at 750° C. and 1000° C.

| Aerosil content [wt. %] | Glass content [wt. %] | Calcination temperature [° C.] | Density [g/cm³] | Spec. surface [m²/g] | Spec. pore volume [mm³/g] |
| --- | --- | --- | --- | --- | --- |
| 90 | 10 | 750 | 2.31 | 74 | 1628 |
| 90 | 10 | 1000 | 2.32 | 61 | 1331 |
| 75 | 25 | 750 | 2.38 | 62 | 1510 |
| 75 | 25 | 1000 | 2.37 | 30 | 789 |

The results of these investigations can be summarized as follows:

The density is dependent only on the percentage by volume of glass, and so not on the calcination temperature.

There is a reduction in the specific surface and the specific pore volume both with the percentage by mass of glass and with the calcination temperature.

The linear reduction in specific surface and specific pore volume with increasing glass content is steeper at higher calcination temperatures.

2. Other Hybrid Particles 2.2 Hybrid particles with mixed-oxide aerosils

Instead of the Aerosils, mixed-oxide Aerosils can be used which contain e.g. $Al_2O_3$. Two $SiO_2/Al_2O_3$ sols of differing composition were produced for this. MOX F223 (16 wt. % $Al_2O_3$) and VP MOX 90 (61 wt. % $Al_2O_3$) were used as educts. The MOX Aerosils are worked into water using an ultraturrax and the sols are placed in a shaker overnight. The $SiO_2/Al_2O_3$ sols are each mixed with a glass suspension in an MOX Aerosil:glass ratio of 1:1. Spray drying at temperatures below 200° C. followed by calcination produces hybrid particles in which the glass particles are distributed virtually homogeneously in the MOX Aerosil matrix.

2.2 Hybrid particles containing glass, fluoroapatite and zirconium dioxide

Instead of an amorphous glass with particle sizes of approx. 1 μm, finer glasses can also be used, and also crystalline compounds such as fluoroapatite or zirconium dioxide. For this purpose, Aerosil 90® sols were mixed with a glass suspension (particle size approx. 0.7 μm) in an Aerosil 90®:glass ratio of 1:1 and with suspensions of fluoroapatite or zirconium dioxide in an Aerosil 90®:crystalline compound ratio of 3:1. Spray drying at temperatures below 200° C. followed by calcination produces spherical hybrid particles in which the glass, the fluoroapatite or the zirconium dioxide is distributed virtually homogeneously in the Aerosil matrix.

Further variations and modifications of the foregoing will be apparent to those skilled in the art and are intended to be encompassed by the claims appended hereto.

German priority application 100 42 050.8 is relied on and incorporated herein by reference.

We claim:

1. A dental material comprising:

a polymerizable binder, a catalyst for cold-, heat- and/or photo-polymerization of said binder, and 0.5–75 wt. % based on the total weight of the dental material of a hybrid filler (A)

and 0.0–95 wt. % based on the total weight of the dental material of other fillers (B) together with 0.0–2 wt. % of other conventional additives (C), wherein the hybrid filler (A) consists of a sintered heterogeneous mixture of fillers (B) and one or more primary particles of oxides, fluorides, sulfates, phosphates, borides, nitrides, carbides and/or silicides of elements of Groups I to V of the Periodic Table of Elements, wherein the pore volume of hybrid filler (A) is >0–2000 mm$^3$/g, wherein the pore diameter of hybrid filler (A) is >0–1000 nm.

2. The dental material according to claim 1 wherein the polymerizable binder is an ethylenically unsaturated monomer, epoxide, ormocer, liquid crystalline monomer, oxethane, spiroorthoester or -carbonate.

3. The dental material according to claim 1, wherein the hybrid filler (A) has a size of 1–200 μm.

4. The dental material according to claim 1, wherein the hybrid filler (A) has a size of 3–90 μm.

5. The dental material according to claim 1 wherein the size ratio between the fillers (B) contained in filler (A) and one or more primary particles of oxides, fluorides, sulfates, phosphates, borides, nitrides, carbides and/or suicides of elements of Groups I to V of the Periodic Table of Elements is in the range >1:1–1:20000.

6. The dental material according to claim 2 wherein the size ratio between the fillers (B) contained in filler (A) and one or more primary particles of oxides, fluorides, sulfates, phosphates, borides, nitrides, carbides and/or silicides of elements of Groups I to V of the Periodic Table of Elements is in the range >1:1–1:20000.

7. The dental material according to claim 3 wherein the size ratio between the fillers (B) contained in filler (A) and one or more primary particles of oxides, fluorides, sulfates, phosphates, borides, nitrides, carbides and/or silicides of elements of Groups I to V of the Periodic Table of Elements is in the range >1:1–1:20000.

8. The dental material according to claim 1 wherein the size ratio between the fillers (B) contained in filler (A) and one or more primary particles of oxides, fluorides, sulfates, phosphates, borides, nitrides, carbides and/or silicides of elements of Groups I to V of the Periodic Table of Elements is in the range 1:10–1:1000.

9. The dental material according to claim 1 wherein the ratio of the mass of the fillers (B) contained in filler (A) to one or more primary particles of oxides, fluorides, sulfates, phosphates, borides, nitrides, carbides and/or silicides of elements of Groups I to V of the Periodic Table of Elements is in the range 25–75 wt. % of (B) in relation to the total weight of (A).

10. The dental material according to claim 2 wherein the ratio of the mass of the fillers (B) contained in filler (A) to one or more primary particles of oxides, fluorides, sulfates, phosphates, borides, nitrides, carbides and/or silicides of elements of Groups I to V of the Periodic Table of Elements is in the range 25–75 wt. % of (B) in relation to the total weight of (A).

11. The dental material according to claim 3 wherein the ratio of the mass of the fillers (B) contained in filler (A) to one or more primary particles of oxides, fluorides, sulfates, phosphates, borides, nitrides, carbides and/or silicides of elements of Groups I to V of the Periodic Table of Elements is in the range 25–75 wt. % of (B) in relation to the total weight of (A).

12. The dental material according to claim 1 wherein the pore volume of hybrid filler (A) is 50–1500 mm$^3$/g.

13. The dental material according to claim 2 wherein the pore volume of hybrid filler (A) is 50–1500 mm$^3$/g.

14. The dental material according to claim 1 wherein the pore diameter of hybrid filler (A) is preferably 20–100 nm.

15. The dental material according to claim 2 wherein the pore diameter of hybrid filler (A) is 20–100 nm.

16. The dental material according to claim 1 wherein said hybrid filler (A) is loaded with a polymerizable or polymerized binder.

17. The dental material according to claim 2 wherein said hybrid filler (A) is loaded with a polymerizable or polymerized binder.

18. The dental material according to claim 16 wherein said binder is an ethylenically unsaturated monomer, epoxide, ormocer, liquid crystalline monomer, oxethatne, spiroorthoester or -carbonate.

19. The dental material according to claim 1 wherein hybrid filler (A) contains primary particles of oxides, fluorides, sulfates and/or phosphates of elements of Groups I to V of the Periodic Table of Elements.

20. The dental material according to claim 2 wherein hybrid filler (A) contains primary particles of oxides, fluorides, sulfates and/or phosphates of elements of Groups I to V of the Periodic Table of Elements.

21. A process for the production of a dental material comprising:

mixing together a polymerizable binder, a catalyst for cold-, heat-, or photo-polymerization and 0.5–75 wt. % in relation to the dental material of a hybrid filler (A) and 0.0–95 wt. % in relation to the dental material of other fillers (B) and 0.0–2 wt. % of other conventional additives (C) wherein hybrid filler (A) is prepared by sintering a mixture of filler (B) and one or more primary particles of oxides, fluorides, sulfates, phosphates, borides, nitrides, carbides and/or silicides of elements of Groups I to V of the Periodic Table of Elements, wherein before sintering, hybrid filler (A) is spray dried at <200° C.

22. The process according to claim 21 wherein said polymerizable binder is an ethylenically unsaturated monomer, epoxide, ormocer, liquid crystalline monomer, oxethane, spiroorthoester or spiroorthocarbonate.

23. The process according to claim 21 wherein hybrid filler (A) is sintered at >500° C. and <1500° C.

24. The process according to claim 23 wherein the hybrid filler (A) is sintered at >700° C. and <1200°°C.

25. The process according to claim 21, wherein said hybrid filler (A) is spray dried at <130° C.

26. The process according to claim 21 further comprising loading porous hybrid filler (A) with a polymerizable or polymerized binder, by loading with a gaseous or liquid monomer and then polymerizing in said filler.

27. The process according to claim 26 wherein said binder is formed from an ethylenically unsaturated monomer, epoxide, ormocer, liquid crystalline monomer, oxethane, spiroorthoester or -carbonate.

28. A dental material which is obtained by the process of claim 21.

29. A dental material which is obtained by the process of claim 22.

30. A dental material which is obtained by the process of claim 26.

31. Hybrid filler (A), comprising a sintered heterogeneous mixture of a filler (B) and one or more primary particles of oxides, fluorides, sulfates, phosphates, borides, nitrides, carbides and/or silicides of elements of Groups I to V of the Periodic Table of Elements, wherein the pore volume of hybrid filler (A) is >0–2000 mm$^3$/g, wherein the pore diameter of hybrid filler (A) is >0–1000 nm.

32. A porous hybrid filler (A) comprising a sintered heterogeneous mixture of filler (B) and one or more primary particles of oxides, fluorides, sulfates, phosphates, borides, nitrides, carbides and/or silicides of elements of Groups I to V of the Periodic Table of Elements, loaded with a polymerizable or polymerized monomer.

33. The porous hybrid filler (A) according to claim 32 wherein said monomer is an ethylenically unsaturated monomer, epoxide, ormocer, liquid crystalline monomer, oxethane, spiroorthoester or -carbonate.

34. The porous hybrid filler (A) according to claim 32 wherein filler B is silica.

35. The dental material according to claim 1 wherein filler B is silica.

36. A dental material composition comprising a polymerizable monomer as a binder ethylenically unsaturated monomer, epoxide, ormocer, liquid crystalline monomer, oxethane, spiroorthoester or -carbonate, a catalyst for cold-, heat- and/or photo-polymerization of said binder and 0.5–75 wt. % based on the dental material of a hybrid filler (A) and 0.0–95 wt. % based on the dental material of other fillers (B), wherein hybrid filler (A) comprises a sintered heterogeneous mixture of at least one filler (B) and one or more primary particles of an oxide, fluoride, sulfate, phosphate, boride, nitride, carbide or silicide of an element selected from Group I to V of the Periodic Table of Elements, said filler B being selected from the group consisting of microfine, pyrogenic or precipitated silica, wherein the pore volume of hybrid filler (A) is >0–2000 mm$^3$/g, wherein the pore diameter of hybrid filler (A) is >0–1000 nm.

37. A dental material composition comprising a polymerizable monomer as a binder ethylenically unsaturated monomer, epoxide, ormocer, liquid crystalline monomer, oxethane, spiroorthoester or -carbonate, a catalyst for cold-, heat- and/or photo-polymerization of said binder and 0.5–75 wt. % based on the dental material of a hybrid filler (A) and 0.0–95 wt. % based on the dental material of other fillers (B), wherein hybrid filler (A) comprises a sintered heterogeneous mixture of at least one filler (B) and one or more primary particles of an oxide, fluoride, sulfate, phosphate, boride, nitride, carbide or silicide of an element selected from Group I to V of the Periodic Table of Elements, said filler (B) being selected from the group consisting of glass, TiO$_2$, zirconium oxide and fluoroapatite particles, wherein the pore volume of hybrid filler (A) is >0–2000 mm$^3$/g, wherein the pore diameter of hybrid filler (A) is >0–1000 nm.

38. A process for the production of a dental material comprising:

mixing together a polymerizable binder, a catalyst for cold-, heat-, or photo-polymerization and 0.5–75 wt. % in relation to the dental material of a hybrid filler (A) and 0.0–95 wt. % in relation to the dental material of other fillers (B) and 0.0–2 wt. % of other conventional additives (C), wherein hybrid filler (A) is prepared by sintering a mixture of filler (B) and one or more primary particles of oxides, fluorides, sulfates, phosphates, borides, nitrides, carbides and/or silicides of elements of Groups I to V of the Periodic Table of Elements, wherein hybrid filler (A) is sintered at >500° C. and <1500° C., wherein before sintering, hybrid filler (A) is spray dried at <200° C.

39. A process for the production of a dental material according to claim 38, wherein before sintering, hybrid filler (A) is spray dried at <130° C.

40. A process for the production of a hybrid filler comprising:

sintering together a filler and one or more oxides, fluorides, sulfates, phosphates, borides, nitrides, carbides and/or silicides of elements of Groups I to V of the Periodic Table of Elements to form the hybrid filler, wherein the hybrid filler has a pore volume of 50–1500 mm$^3$/g and a pore diameter of 20–100 nm.

* * * * *